United States Patent

Lurz

[11] Patent Number: 5,569,164
[45] Date of Patent: Oct. 29, 1996

[54] SURGICAL LAPAROSCOPIC APPARATUS

[75] Inventor: Michael Lurz, Dürbheim, Germany

[73] Assignee: Delma elektro- und medizinische Apparatebau Gesellschaft mbH, Tuttlingen, Germany

[21] Appl. No.: 336,370

[22] Filed: Nov. 8, 1994

[30] Foreign Application Priority Data

Nov. 24, 1993 [DE] Germany ............ 43 40 056.6

[51] Int. Cl.⁶ .................................................. A61B 1/00
[52] U.S. Cl. ............................ 600/158; 606/46; 606/41; 606/1; 607/104; 604/21
[58] Field of Search ............................... 606/1, 41, 42, 606/45–52, 205–208; 600/156–158; 607/101–104; 604/21, 22

[56] References Cited

U.S. PATENT DOCUMENTS

| 4,261,343 | 4/1981 | Ouchi et al. ............ 600/158 |
| 4,535,773 | 8/1985 | Yoon . |
| 4,567,880 | 2/1986 | Goodman . |
| 5,027,791 | 7/1991 | Takahashi ................ 600/158 |
| 5,254,117 | 10/1993 | Rigby et al. ............. 606/46 |
| 5,456,684 | 10/1995 | Schmidt et al. ........... 606/41 |

FOREIGN PATENT DOCUMENTS

| 0463363 | 1/1992 | European Pat. Off. . |
| 0518051 | 12/1992 | European Pat. Off. . |
| 3200724 | 8/1983 | Germany . |
| 3844131 | 7/1989 | Germany . |
| 4036509 | 2/1992 | Germany . |
| 9210590 U | 2/1993 | Germany . |
| 4242143 | 6/1994 | Germany . |

*Primary Examiner*—Angela D. Sykes
*Assistant Examiner*—Michael Peffley
*Attorney, Agent, or Firm*—Townsend and Townsend and Crew

[57] ABSTRACT

A surgical laparoscopic apparatus comprises a protector tube (11) and a handgrip (12) mounted onto the rear end thereof. At least one rod-shaped instrument (13) is arranged in an axially removable way in an axial guide channel (14) provided in the protector tube (11) and the handgrip (12). A dual purpose flushing/suction channel (15) extends parallel thereto in the protector tube (11) and partially also in the handgrip (12) and passes through the handgrip (12) to external flush and suction connectors (16, 17). A twin-position three-way valve (19) is arranged in the handgrip adjacent to the guide channel (14) and, in the one position, connects the flushing/suction channel (15) to the flush and suction connectors (16, 17) and, in the other position, connects the guide channel (14) to the flush connector or suction connector (16, 17).

6 Claims, 2 Drawing Sheets

SURGICAL LAPAROSCOPIC APPARATUS

BACKGROUND OF THE INVENTION

The invention relates to a surgical laparoscopic apparatus, and in particular to a multi-functional treatment apparatus formed as a piece of hand-held equipment.

Multi-functional treatment apparatuses of this kind are known for example from DE-OS 42 42 143. They have at least two channels in the axial direction, one for a removable operating tool and one acting as a dual function flushing/suction channel. A tube for the receipt of radio frequency supply leads can for example be inserted into the tool guide channel and for example carry two pliers-like coagulation electrodes at its distal end which can be brought together. The flushing/suction channel can be connected via the flushing liquid supply connector or suction connector to a flushing liquid supply or to a suction pump respectively so that selectively either flushing liquid can be fed through the channel or liquid from a wound site sucked out through the channel.

The protector tube of apparatuses of this kind should have a cross-section which is as small as possible in order to be able to reach an operation site unhindered, for example through a trocar. However, on the other hand, the guide channel must have a certain minimum cross-section in view of the pre-specified cross-section of the rod-shaped instrument. Thus in general there is little space remaining in the protector tube and handgrip for the flushing/suction channel so that it has a comparatively small cross-section.

The amount of flushing liquid which can be supplied, or the amount of secretions from the operation site which can be sucked away through this channel are limited. It has proved to be particularly disadvantageous that blockages can easily occur with particulate material sucked out from the operation site as a result of the small cross-section of the channel in the protector tube.

SUMMARY OF THE INVENTION

It is an object of the invention to provide a surgical laparoscopic apparatus of the initially named kind which, in particular, should be able to transfer more flushing liquid or sucked out liquid without increasing the cross-section of the protector tube and effectively to avoid blockages.

The idea underlying the invention is the realization that, when the instrument is removed, the guide channel which generally has a considerably larger cross-section than the flushing/suction channel can be made available, at least in the region of the protector tube, as an additional supply or removal channel for flushing liquid by connecting the guide channel to the flush connector or suction connector respectively via a valve which preferably switches automatically. In this manner, the guide channel which extends through the protector tube and at least partially through the handgrip is also available for flushing or suction purposes. When the surgeon works with the instrument removed, the guide channel, which is primarily provided for the instrument, automatically becomes available for flushing and suction, i.e. no conscious actions on the part of the surgeon are required.

If, during an operation and while an instrument is inserted into the guide channel, the surgeon establishes that the regular flushing/suction channel does not have sufficient capacity, or is even blocked, he can remedy this by removing the instrument which connects up the guide channel to the flush connector or to the suction connector respectively. The range of possible applications of the apparatus of the invention are therefore considerably more universal since the cross-section in the region of the protector tube which accesses the operation site has not been enlarged.

The instrument can also be formed from an endoscope fed through the guide channel.

BRIEF DESCRIPTION OF THE DRAWINGS

The invention is described in the following by means of example only with the aid of the drawings.

DESCRIPTION OF THE PREFERRED EMBODIMENTS

Figure 1:
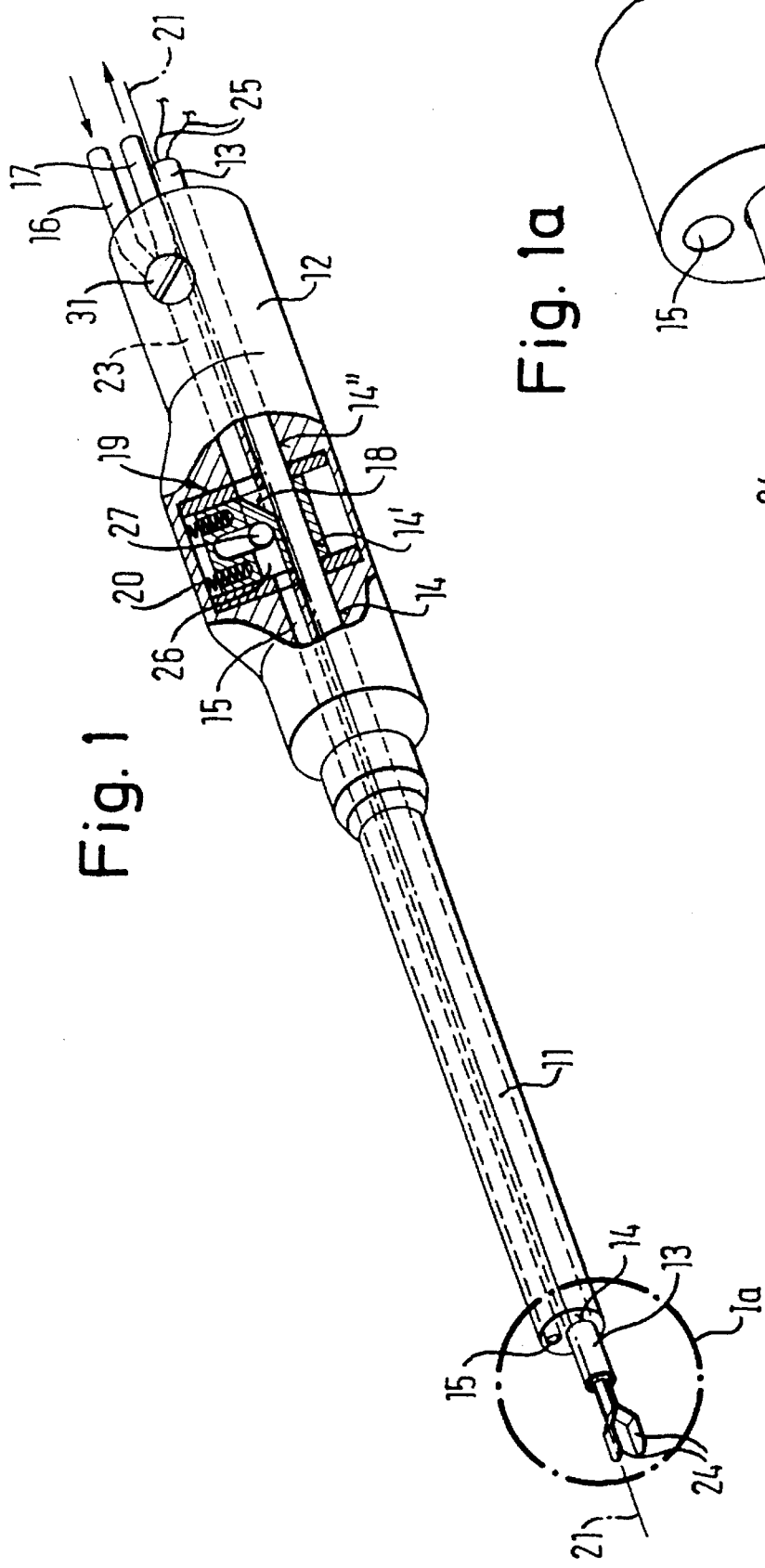
FIG. 1 is a schematic perspective view of the surgical laparoscopic apparatus of the invention, wherein in the handgrip a twin-position three-way valve is illustrated schematically in section.
Figure 1A:
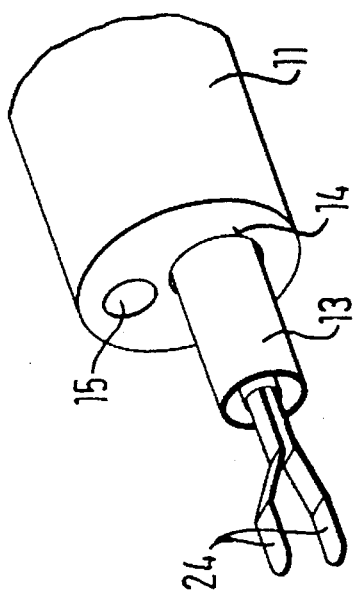
FIG. 1a shows the region of in FIG. 1 outlined by phantom line Ia in enlarged form.

In accordance with FIG. 1, the surgical laparoscopic apparatus of the invention comprises a handgrip 12 on whose front end a protector tube 11 is secured, preferably releasably. A central axial guide channel 14 is arranged in the handgrip and, parallel and adjacent thereto, a flushing/suction channel 15. This is shown in FIG. 1 and FIG. 1a. The channels 14, 15 continue into the handgrip 12 in the manner shown in FIG. 1 and open out initially into a twin-position three-way valve 19 built into the handgrip 12. This handgrip is shown enlarged in FIGS. 2 and 3. In the position of the valve 19 illustrated in FIGS. 1 and 2 in which the instrument is installed, the guide channel 14 passes through a bore 14' in a slider 22 (described below) into a channel 14" arranged behind it of the same cross-section. A rod-shaped instrument 13 is guided in from the rear end of the handgrip 12 through the channels 14, 14', 14" in such a manner that it extends beyond the front end of the protector tube 11 with its distal end, this being provided with two coagulation electrodes 24.

Two electric leads 25 for guiding radio frequency voltage can be connected to the rear end of the rod-shaped instrument 13 as shown FIG. 1. The electrical leads 25 supply the coagulation electrodes 24 with a suitable radio frequency coagulation current.

The valve 19 comprises a bushing 34 secured in a transverse bore in the handgrip 12 and a slider 22 accommodated in the bush with a push fit.

Figure 2:
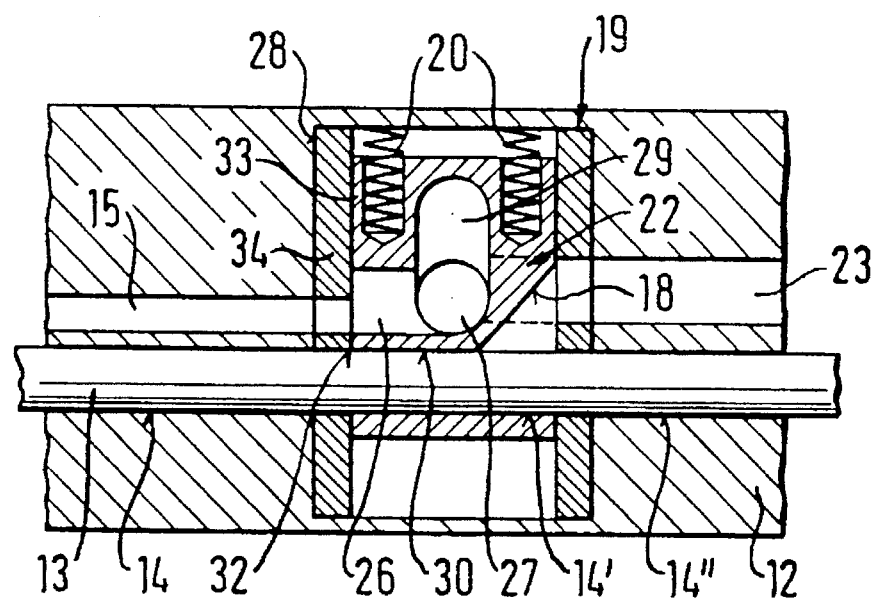
FIG. 2 is an enlarged sectional view of the twin-position three-way valve shown in section in FIG. 1 when the instrument is inserted.

As shown in FIGS. 1 and 2, the slider 22 has a channel portion 26 with an enlarged cross-section which is connected to the rear opening of the flushing/suction channel 15, this cross-section being the same or larger than that of the guide channel 14. The channel portion 26 adjoins at the rear to a transverse slot or elongate hole 29, the cross-section of the transverse slot 29 being at least as large as that of the guide channel 14 and also situated in the slider 22.

A transverse bore 27 is arranged in the handgrip 12 and has the same cross-sectional size as the channel portion 26. The transverse bore 27 extends perpendicular to the direction of and laterally aligned to the transverse slot 29.

The transverse bore 27 is connected up to a connector channel 23 inside the handgrip 12 and extends approximately as a prolongation of the flushing/suction channel 15, with the connector channel 23 having a cross-section which is at least the same as that of the guide channel 14.

The transverse slider 22 is biased by a coil spring 20 in the direction of the rod-shaped instrument 13 which, in FIG. 1, is arranged adjacent to the transverse slider 22 so that, when the operating tool is inserted, the surface 30 of the slider 22 which is adjacent to the instrument 13 is in contact with the operating tool 13 with a push fit as shown in FIG. 1 and FIG. 2.

The connector channel 23 leads to switching valve 31 provided in the rear end of the handgrip 12 (FIG. 1). The switching valve can be actuated externally in a manner which is not shown and permits the connector channel 23 to be selectively connected either to an external flush connector 16 or to an external suction connector 17. Pipes can be connected up to the connectors 16, 17 which are either supplied with a flushing liquid or connected to a suction pump respectively.

The mode of operation of the instrument described above is as follows:

In the working or operating position shown in FIG. 1 and FIG. 2, the operational tip of the rod-shaped instrument 13 extends beyond the front end of the protector tube 11 and an operation can be performed by means of the coagulation electrodes 24. Using actuating means (not shown) the electrodes 24 can be pulled back inside the rod-shaped instrument 13 causing a pliers-like movement of the electrodes together.

During or after the operation flushing, water can be conducted into the operation site in front of the tip of the protector tube 11 through the flushing water connector 16 via the valves 31, 19 and the flushing water channel 15. By switching the valve 31 into the suction position, liquid can be sucked out from the operation site through the suction channel 15 and the valves 19, 31 via the suction connector 17. In the operating position illustrated in FIG. 1 and FIG. 2, the slider 22 is held via the instrument 13 in the position where it is pushed back against the force of the springs 20 and in which the flushing/suction channel 15 is aligned with the channel portion 26 while the guide channel 14 opposite the channel portion 26 is sealed off by the sealing edge 32.

Figure 3:
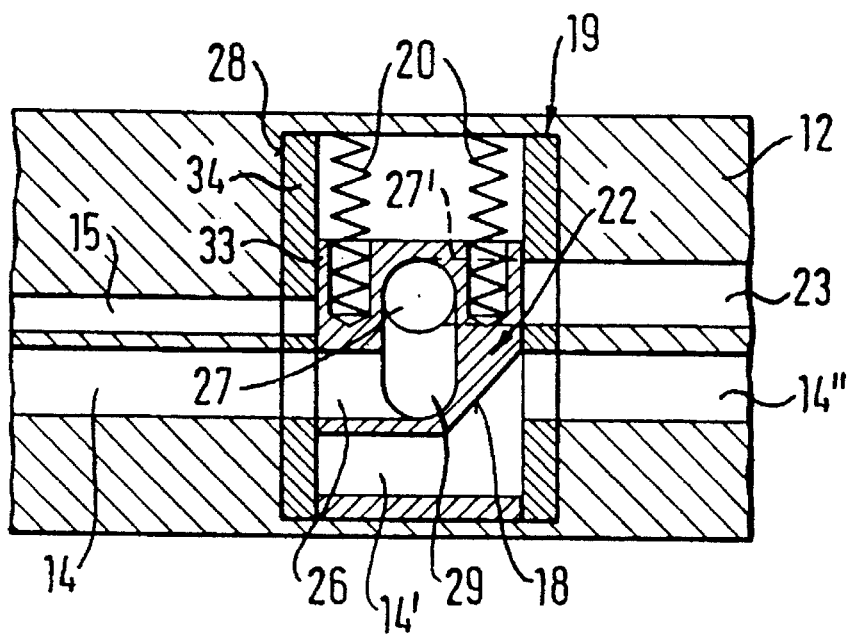
FIG. 3 is a sectional view corresponding to that of FIG. 2 when the instrument is removed.

If the rod-shaped instrument 13 is axially withdrawn from the position of FIG. 2, the springs 20 press the slider 22 out of the position of FIG. 2 into that of FIG. 3 thereby moving the channel portion 26 into axial alignment with the guide channel 14 and sealing off the end of the flushing/suction channel 15 with a flange 33 of the slider 22.

In this manner, the flow connection between the flushing/suction channel 15 and the transverse bore 27 is interrupted and the part of the guide channel 14 situated in front of the valve 19 is connected up to the valve 31 as shown in FIG. 1 via the channel portion 26 of the same cross-section, the transverse slot 29, the transverse bore 27 and the connector channel 23. By suitably positioning the valve 31, the guide channel 14 can now be selectively connected to the flush connector 16 or to the suction connector 17.

This is particularly advantageous when sucking out secretions from the operation site since when doing this larger particles are often sucked out with the fluid and could block the narrow suction channel 15. The danger of blocking is substantially smaller in the guide channel 14 due to its considerably larger cross-section.

Although the small cross-section of the flushing/suction channel 15 inside the protector tube 11 follows from its function, there is no difficulty in making the cross-sections of the channel portion 26, the transverse bore 27, the transverse slot 29 and the subsequent connector channel 23 sufficiently large to ensure that the flow cross-section predefined by the guide channel 14 is not narrowed down any further.

In the valve position of FIG. 3, an inclined surface 18 provided at the rear end of the transverse slider 22 extends transversely over the rear continuation 14" of the guide channel 14. If now the instrument 13 is pushed from the rear end of the handgrip 12 through the continuation 14" its front end engages the inclined surface 18 thereby producing a force which laterally displaces the transverse slider 22 against the bias force of the spring arrangement 20 until the channel portion 26 is axially aligned once more with the flushing/suction channel 15 and until the channel portion 14' provided in the transverse slider 22 adjacent to the channel portion 26 is axially aligned once more with the guide channel 14. Pushing the instrument 13 into the guide channel 14 right up to the position shown in FIG. 1 can now be completed whereupon the instrument 13 can be set in the desired axial position by fixing means (not shown). The flush and suction connectors 16, 17 are now once again flow-connected to the flushing/suction channel 15.

In the preceding description, the switching valve 31 is described as being arranged in the handgrip 12. There is however also the option of accommodating the switching valve outside the handgrip, for example in supply equipment belonging to a hand-held apparatus or in a separate switching unit with the switching valve being controllable via a button provided in the handgrip or at another suitable location and via electrical switching means.

If the switching valve is provided outside the handgrip 12, a single connector 16, 17 is sufficient in order to be able to selectively supply flushing liquid to or to suck off liquid from the operation region.

Although in FIG. 1 the connectors 16, 17 are illustrated as emerging longitudinally from the rear end of the handgrip 12, it is preferred to bring out the connectors 16, 17 transversely from the handgrip 12 at the height of the valve.

List of Reference Numerals 11 protector tube
12 handgrip
13 instrument
14 guide channel
15 flushing/suction channel
16 flush connector
17 suction connector
18 inclined surface
19 twin-position three-way valve
20 bias spring
21 axis
22 slider
23 connector channel
24 coagulation electrode
25 electrical leads
26 channel portion
27 transverse bore
28 transverse bore
29 transverse slot 30 surface
31 switching valve
32 sealing edge
33 flange
34 bush

What is claimed is:

1. Surgical laparoscopic apparatus comprising a handgrip, and a protector tube mounted onto a front end thereof, an axial guide channel formed in the protector tube and the handgrip for axially movably receiving at least one rod-shaped instrument, a flushing and suction channel extending through the handgrip and the protector tube, a flush and suction connector operatively associated with the handgrip, and a twin-position three-way valve arranged in the handgrip adjacent the guide channel and fluidly coupled to the guide channel, the flushing and suction channel and the flush and suction connector which, in first position, connects the flushing and suction channel to the flush and suction connector and, in a second position, connects the guide channel to the flush and suction connector.

2. Apparatus in accordance with claim 1 including self-actuating switching means for displacing the valve into the first position in which the flushing and suction channel is connected to the flush and suction connector when the instrument is inserted into the guide channel and for displacing the valve into the second position in which the valve connects the guide channel to the flush and suction connector when the instrument is removed from the guide channel.

3. Apparatus in accordance with claim 1 including means for biasing the valve towards the second position in which it connects the guide channel to the flush and suction connector, and positioning means for switching the valve against the biasing into the first position in which the valve connects the flushing and suction channel to the flush and suction connector when the instrument is inserted into the guide channel.

4. Apparatus in accordance with claim 1 wherein the valve has a slider extending transversely to an axis of the instrument, a spring arrangement biasing the slider to a position in which the guide channel is connected to a connector channel leading to the flush and suction connector and which protrudes into the guide channel when in this position, and an inclined surface provided on the slider and aligned with the guide channel so that the insertion of the rod-shaped instrument causes a displacement of the slider against a bias force of the spring arrangement into a position in which the slider connects the flushing and suction channel to the connector channel.

5. Apparatus in accordance with claim 1, including a switching valve for selectively connecting one of the flush connector and the suction connector to the three-way valve in the handgrip.

6. Surgical laparoscopic apparatus comprising a handgrip and a protector tube projecting from a front end of the handgrip, a first channel formed in the protector tube and the handgrip adapted for slidably receiving a rod-shaped instrument, a flushing and suction channel formed in the protector tube and the handgrip, a flush and suction connector associated with the handgrip, and a three-way valve fluidly connecting the guide channel, the flushing and suction channel, and the flush and suction connector so that the flush and suction connector can optionally be connected to the guide channel and the flushing and suction channel by moving the valve between respective first and second valve positions.

* * * * *